United States Patent [19]

Pieper

[11] Patent Number: 4,645,835

[45] Date of Patent: Feb. 24, 1987

[54] PROCESS FOR MAKING CHLOROISOCYANURIC ACIDS

[75] Inventor: Werner Pieper, Kerpen, Fed. Rep. of Germany

[73] Assignee: Hoechst Aktiengesellschaft, Fed. Rep. of Germany

[21] Appl. No.: 748,022

[22] Filed: Jun. 24, 1985

[30] Foreign Application Priority Data

Jul. 6, 1984 [DE] Fed. Rep. of Germany ....... 3424823

[51] Int. Cl.$^4$ .................. C07D 251/28; C07D 251/26
[52] U.S. Cl. ..................................... 544/190; 544/218
[58] Field of Search ............................... 544/190, 218

[56] References Cited

U.S. PATENT DOCUMENTS

| | | | |
|---|---|---|---|
| 2,969,360 | 1/1961 | Westfall | 544/192 |
| 3,222,138 | 12/1965 | Becanne et al. | 544/190 |
| 3,668,204 | 6/1972 | Mesiah | 544/190 |
| 3,878,208 | 4/1975 | Carlson et al. | 544/190 |
| 4,395,548 | 7/1983 | Start | 544/190 |

FOREIGN PATENT DOCUMENTS 1072625  7/1960  Fed. Rep. of Germany.
1141641  7/1963  Fed. Rep. of Germany.
1388936  3/1975  United Kingdom.

OTHER PUBLICATIONS

Linder, Fette/Seife/Anstrichmittel, 63, 451 (1961).

*Primary Examiner*—John M. Ford
*Attorney, Agent, or Firm*—Connolly and Hutz

[57] ABSTRACT

Chloroisocyanuric acids are made by reacting an aqueous suspension of cyanuric acid while stirring with an alkali metal compound in the presence of chlorine gas between 0° and 40° C. at a pH of less than 7. More particularly, the reaction is effected in a system gastightly sealed with respect to the outside; a chlorine gas atmosphere with pressure of more than 500 millibars is established above the continuously renewed (by agitation) surface of the cyanuric acid suspension, and the pressure is maintained; the alkali metal compound is an alkali metal hydroxide solution which is added to the cyanuric acid suspension at a rate sufficient for the resulting reaction mixture to always present a pH of less than 7.

3 Claims, No Drawings

PROCESS FOR MAKING CHLOROISOCYANURIC ACIDS

The present invention relates to a process for making chloroisocyanuric acids by reacting an aqueous cyanuric acid suspension, while stirring, with an alkali metal compound in the presence of chlorine gas at temperatures between 0° and 40° C., preferably between 10° and 20° C., and at a pH of less than 7.

It has been described that chloroisocyanuric acids can be made by reacting an aqueous solution or suspension of a cyanuric acid salt or a cyanuric acid/base-mixture with gaseous or liquid chlorine, the degree of chlorination being determined by the quantitative ratio selected for the cyanuric acid and base (cf. Fette, Seifen, Anstrichmittel 63, 451 (1961)).

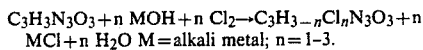

$$C_3H_3N_3O_3 + n\ MOH + n\ Cl_2 \rightarrow C_3H_{3-n}Cl_nN_3O_3 + n\ MCl + n\ H_2O \quad M = \text{alkali metal};\ n = 1\text{-}3.$$

The product obtained is a suspension of chloroisocyanuric acid in an aqueous solution.

As can be inferred from U.S. Pat. No. 2,969,360, the following conditions are deemed optimal for the absorption of chlorine by the reaction mixture: high temperatures, high pH-value, effective distribution of chlorine gas in the reaction mixture and thorough agitation of the reaction solution.

In an alkaline solution, however, the cyanuric acid is subject to an oxidative degradation reaction in accordance with the following equation

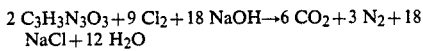

$$2\ C_3H_3N_3O_3 + 9\ Cl_2 + 18\ NaOH \rightarrow 6\ CO_2 + 3\ N_2 + 18\ NaCl + 12\ H_2O$$

so that this particular reaction basically compares unfavorably with the chlorination in an acid phase.

In contrast therewith, the chlorine absorption in an acid solution is not quantitative so that a portion of injected chlorine gas remains unused and is obtained as off-gas. This is the reason why preference is normally given to a two stage process wherein the off-gas coming from the second stage is introduced into an alkaline first chlorination stage in which the educts used, namely cyanuric acid and alkali metal hydroxide, are partially chlorinated, and the partially chlorinated products are completely chlorinated in the second stage.

German Pat. No. 1 072 625 describes a process for making chlorinated cyanuric acids with the use of a very dilute cyanuric acid suspension the pH of which is maintained below 7 during the entire reaction. In this process, the alkali metal hydroxide is, however, replaced by a sodium salt, such as sodium phosphate or sodium acetate, which are used in the stoichimetric ratio necessary for the degree of chlorination targeted, and the pH-value initially selected is adjusted later by the addition of an acid or base to a value determining the degree of chlorination. As a result, a mother liquor additionally loaded with the quantities of salts used (e.g. phosphates, acetates) is invariably obtained together with inevitably forming stoichiometric quantities of chloride, after filtration of the chlorinated cyanuric acid.

In addition, upon the injection of chlorine gas into an alkaline suspension of cyanuric acid containing sodium hydroxide in a proportion necessary for the degree of chlorination targeted, considerable quantities of carbon dioxide and nitrogen are evolved within the region of the neutral point. The reaction gases set free and unreacted chlorine gas transport solid matter particles separating from the reaction mixture to the surface where they form a foam which is difficult to bring back into the suspension; in the end, the reactor outlets become clogged.

As a result, the yield is impaired or insufficiently chlorinated final product is obtained.

We have now unexpectedly found that these difficulties are easy to overcome (a) by effecting the reaction in a system gastightly closed with respect to the outside;

(b) by establishing a chlorine gas atmosphere with a pressure of more than 500 millibars, preferably of 1063 to 1513 millibars, above the continuously renewed (by agitation) surface area of the cyanuric acid suspension and by maintaining the pressure during the reaction; and (c) by using, as the alkali metal compound, an alkali metal hydroxide solution and by metering it into the cyanuric acid suspension at a rate sufficient for the resulting reaction mixture always to present a pH of less than 7.

In clear contrast with all standard processes of which we are aware, the chlorine is not introduced directly into the cyanuric acid suspension but only into the gas chamber of the reactor so that it is merely absorbed and reacted at the surface of the suspension.

Sodium hydroxide solution should preferably be used as the alkali metal hydroxide solution, and the reaction temperature should conveniently be maintained at 0°–40° C., preferably 10°–20° C., by cooling the reactor.

The process of this invention compares favorably with prior art methods in respect of the following points:

There is no formation of gaseous by-products, especially carbon dioxide and nitrogen, as the pH-value of the reaction mixture always remains in the acid region so that it is not possible for the above decomposition reaction to occur.

There is no need for the sodium hydroxide solution to be used in overrated dosages (as incidentally suggested in U.S. Pat. No. 2,969,360) to obtain complete chlorination as alkali is not consumed in side reactions.

Chlorine gas is not injected into the suspension but absorbed only at the surface of the mixture, nor are $CO_2$ and $N_2$ obtained as decomposition products; as a result, annoying foam is definetely prevented from forming. Despite this, the reaction occurs at high velocity due to the continuously renewed (by agitation) suspension surface.

The single stage process of this invention calls for little expenditure of apparatus. Use can be made of a relatively small dimensioned reactor needing no additional safety reservoir for foam.

Despite the fact that the reaction is carried out in an acid reaction mixture, the chlorine yield is quantitative as chlorine gas is not liable to escape into the atmosphere from the gas-tightly sealed reaction system.

A pressure valve or sealing means, for example, can be used for gastightly sealing the reaction system so that it is possible for the chlorination to be effected at a constant pressure, preferably under slight overpressure.

At a constant stirring velocity and under constant pressure, the chlorine absorption is proportional to the supplied metered quantities of alkali metal hydroxide. The quantitative ratio between absorbed chlorine and alkali metal hydroxide added should be 0.9–1.1 during the entire reaction.

The yield of chloroisocyanuric acid is practically quantitative and limited by the solubility of the final product in the mother liquor, only.

The reaction components should be used in concentrations necessary for the material which is to undergo reaction to remain well stirrable during the entire reaction. To ensure this, it is good practice to use a cyanuric acid suspension of about 10–20% strength as feed material and to prepare a chloroisocyanuric acid suspension of about 10–20% strength as the final product.

In the case of dichloroisocyanuric acid it is possible to prepare the corresponding salt in known manner by neutralization with an aqueous base, such as sodium hydroxide solution.

The following Examples illustrate the invention which is naturally not limited thereto.

EXAMPLE 1

1 kg (7.75 mol) cyanuric acid in form of a 16.7 wgt. % aqueous suspension was placed under a chlorine atmosphere of about 1113 millibar in a 10 l multi-necked flask provided with an agitator, dropping funnel, inside thermometer and connection to a chlorine gas bottle. The reaction system was sealed with respect to the environment using a water-filled sealing means allowable for a maximum pressure of about 1215 millibar. Next, 1550 g sodium hydroxide solution of 40% strength was metered into the agitated suspension while cooling to 10°–20° C. at a constant rate of 17 g per minute, the chlorine gas being admitted so that the pressure in the reaction system remained constant. 1100 g (15.5 mol) chlorine was consumed within 100 minutes whereupon the suspension ceased to absorb further chlorine gas. The product was filtered off, water-washed and dried. The yield was 1421 g (7.2 mol) dichloroisocyanuric acid, corresponding to 92.9% of the theoretical, with an active chlorine content of 70.5%.

EXAMPLE 2

A suspension of 645.5 g (5 mol) cyanuric acid in 3230 g water was stirred while cooling to 10°–20° C. in a chlorine atmosphere of about 1113 millibar, in an apparatus as claimed in Example 1. 1500 g sodium hydroxide solution of 40 wgt % strength was added at a regular rate of 10.8 g per minute, 7.4 g chlorine was absorbed per minute so that a total of 1100 g chlorine (15.5 mol) was found to have been absorbed after about 150 minutes, and the reaction was complete. The quantitative ratio of chlorine absorbed and sodium hydroxide solution added was 0.9–1.1 during the entire reaction. 1090 g (4.7 mol) trichloroisocyanuric acid was filtered off, corresponding to a yield of 94%.

EXAMPLE 3 (Comparative Example)

1024 g (7.94 mol) cyanuric acid in 6040 g water and 667 g (16.7 mol) sodium hydroxide solution (5.2 wgt. % excess) were introduced in a chlorine atmosphere of 1063 millibars, into an apparatus as described in Example 1. The agitator was taken into use and 0.8 mol chlorine per mol cyanuric acid was absorbed within 45 minutes. The chlorine was thereafter found to be absorbed at a drastically reduced rate. The decoloration in the gas space above the reaction mixture indicated the formation of a colorless gas which was found to hinder the absorption of chlorine. Only after the foreign gas had been repeatedly allowed to escape was it possible to continue the chlorination until the foreign gas ceased to be evolved at a conversion rate of about 1.5 mol chlorine per mol cyanuric acid. Altogether 20 liter off-gas was collected: gas chromatography showed that it consisted of carbon dioxide and nitrogen. No further foreign gas could be found to be evolved during the further course of the reaction. A total of 1200 g (16.9 mol) chlorine was consumed. 1200 g (6.06 mol) dichloroisocyanuric acid, corresponding to a yield of 76.3%, was obtained.

We claim:

1. In the process for making mono, di- or trichloroisocyanuric acid by reacting an aqueous suspension of cyanuric acid while stirring with an alkali metal compound in the presence of gaseous chlorine at temperatures between 0° and 40° C. at a pH-value of less than 7, the improvement which comprises:
    (a) effecting the reaction in a system gastightly closed with respect to the outside;
    (b) establishing a chlorine gas atmosphere with a pressure of more than 500 millibars above the continuously renewed (by agitation) surface area of the cyanuric acid suspension, and maintaining the pressure during the reaction; and
    (c) using, as the alkali metal compound, an alkali metal hydroxide solution and metering it into the cyanuric acid suspension at a rate sufficient for the resulting reaction mixture always to present a pH of less than 7.

2. The process as claimed in claim 1, wherein a chlorine gas atmosphere corresponding to a pressure of about 1063–1513 millibars is established and maintained.

3. The process as claimed in claim 1, wherein a cyanuric acid suspension of 10–20 weight % strength is used as a feed material.

* * * * *